United States Patent
Blume et al.

(10) Patent No.: US 11,452,477 B2
(45) Date of Patent: Sep. 27, 2022

(54) ELECTROGRAM ANNOTATION SYSTEM

(71) Applicant: SentiAR, Inc., St. Louis, MO (US)

(72) Inventors: Walter Blume, Edwardville, IL (US); Michael K. Southworth, St. Louis, MO (US); Jonathan R. Silva, St. Louis, MO (US); Jennifer N. Avari Silva, St. Louis, MO (US); Ignacio Soriano, Madrid (ES)

(73) Assignee: SentiAR, Inc., St. Louis, MO (US)

( * ) Notice: Subject to any disclaimer, the term of this patent is extended or adjusted under 35 U.S.C. 154(b) by 55 days.

(21) Appl. No.: 17/078,889

(22) Filed: Oct. 23, 2020

(65) Prior Publication Data
US 2021/0121089 A1    Apr. 29, 2021

Related U.S. Application Data

(60) Provisional application No. 62/926,422, filed on Oct. 25, 2019.

(51) Int. Cl.
*A61B 5/339* (2021.01)
*G06F 3/01* (2006.01)
(Continued)

(52) U.S. Cl.
CPC .............. *A61B 5/339* (2021.01); *A61B 5/066* (2013.01); *A61B 5/163* (2017.08); *A61B 5/349* (2021.01); *A61B 5/7203* (2013.01); *A61B 5/749* (2013.01); *G06F 3/011* (2013.01); *G06F 3/013* (2013.01); *G06F 3/017* (2013.01); *G06T 11/60* (2013.01);
(Continued)

(58) Field of Classification Search
CPC ........ G16H 40/63; G16H 50/20; A61B 5/066; A61B 5/339; A61B 5/349; A61B 5/7203; A61B 5/749; A61B 2090/502; A61B 5/7267; G06F 3/013; G06T 2210/41; G06T 11/60; G10L 2015/223; G10L 15/22
See application file for complete search history.

(56) References Cited

U.S. PATENT DOCUMENTS

2004/0193223 A1* 9/2004 Kramer .............. A61N 1/36843
607/9
2005/0209525 A1* 9/2005 Bojovic .................. A61B 5/339
600/512
(Continued)

OTHER PUBLICATIONS

PCT International Search Report and Written Opinion, PCT Application No. PCT/US2020/057098, dated Jan. 27, 2021, 17 pages.

*Primary Examiner* — Phi Hoang
(74) *Attorney, Agent, or Firm* — Fenwick & West LLP

(57) ABSTRACT

In an embodiment, an electrogram (EGM) processing system provides, for display by a head-mounted display (HMD) worn by a user, a holographic rendering of intracardiac geometry. The HMD also displays an electrogram waveform. The EGM processing system determines a gaze direction of the user by processing sensor data from the HMD. The HMD displays a marker overlaid on the electrogram waveform at a location based on an intersection point between the gaze direction and the electrogram waveform. The EGM processing system determines a measurement of the electrogram waveform using the location of the marker. The HMD displays the measurement of the electrogram waveform.

18 Claims, 8 Drawing Sheets

(51) Int. Cl.
*G06T 11/60* (2006.01)
*G10L 15/22* (2006.01)
*A61B 5/06* (2006.01)
*A61B 5/00* (2006.01)
*A61B 5/349* (2021.01)
*G16H 40/63* (2018.01)
*G16H 50/20* (2018.01)
*A61B 5/16* (2006.01)
*A61B 90/50* (2016.01)

(52) U.S. Cl.
CPC .............. *G10L 15/22* (2013.01); *G16H 40/63* (2018.01); *G16H 50/20* (2018.01); *A61B 5/7267* (2013.01); *A61B 2090/502* (2016.02); *G06T 2210/41* (2013.01); *G10L 2015/223* (2013.01)

(56) References Cited

U.S. PATENT DOCUMENTS

| | | | |
|---|---|---|---|
| 2009/0069704 A1* | 3/2009 | MacAdam | G06T 7/0012 600/523 |
| 2012/0035488 A1 | 2/2012 | MacAdam et al. | |
| 2017/0123491 A1* | 5/2017 | Hansen | G06F 3/012 |
| 2018/0200018 A1 | 7/2018 | Silva et al. | |
| 2019/0059770 A1* | 2/2019 | Gunasekar | G16H 30/20 |
| 2019/0065026 A1* | 2/2019 | Kiemele | G06F 3/0488 |
| 2019/0080515 A1 | 3/2019 | Geri et al. | |
| 2019/0183576 A1 | 6/2019 | Fahim et al. | |
| 2019/0250873 A1 | 8/2019 | Blume et al. | |

\* cited by examiner

ELECTROGRAM ANNOTATION SYSTEM

CROSS REFERENCE TO RELATED APPLICATION

This application claims the benefit of priority to U.S. Provisional Application No. 62/926,422, filed on Oct. 25, 2019, which is incorporated herein by reference in its entirety for all purposes.

TECHNICAL FIELD

This disclosure generally relates to the annotation and measurement of electrogram (EGM) information within a medical computing environment.

BACKGROUND

In conventional medical interventional and surgical suites, there are often considerations where one or more operators work in a sterile surgical field while other support personnel are in a separate non-sterile area. The coordinated use of multiple medical systems, e.g., each of which having their own display monitors and user input methods, presents obstacles to efficient use.

In some use cases, the operating physician must maintain a sterile field, and during critical periods of a procedure must maintain one or both hands on medical instruments, e.g., catheters, guidewires, etc. The requirement of sterility may limit the number and type of medical information systems with which the operating physician can interact. The sterility requirement may also limit the interactivity of the medical information systems by requiring sterile bagging procedures that restrict interaction. The requirement of maintaining one or both hands on medical instruments during critical periods of the procedure may preclude the ability for personnel to use conventional medical information system interfaces, e.g., keyboard, mouse, joystick, physical buttons, etc. Electrogram information is often displayed and measured on multiple medical systems, with each system using a different mode of input and output. EGM data includes one or more of time-sampled voltage data, sampling rate, displayed sample rate, assigned color, and sample identifier from electrodes on the body surface or within the heart. Conventional systems present data on display monitors within the procedure and control room. View of the monitor is often hindered due to necessity of physician moving about the room.

SUMMARY

In various embodiments, a method includes providing, for display by a head-mounted display (HMD) worn by a user, a holographic rendering of intracardiac geometry including position of a catheter. The method further includes providing, for display by the HMD, an electrogram waveform generated using data collected from the catheter, wherein the electrogram waveform is displayed adjacent to the holographic rendering. The method further includes determining a gaze direction of the user by processing sensor data from the HMD. The method further includes providing, for display by the HMD, a marker overlaid on the electrogram waveform at a location based on an intersection point between the gaze direction and the electrogram waveform. The method further includes determining a measurement of the electrogram waveform using the location of the marker. The method further includes providing, for display by the HMD, the measurement of the electrogram waveform adjacent to the electrogram waveform.

In an embodiment, determining the measurement of the electrogram waveform using the location of the marker comprises: determining a first position of a first measurement graphic by tracking the location of the marker; determining a second position of a second measurement graphic by tracking the location of the marker; and determining the measurement of the electrogram waveform based on a distance between the first position and the second position.

In an embodiment, the method further includes determining a feature of the electrogram waveform; and responsive to determining that the first position of the first measurement graphic is within a threshold distance from a position of the feature of the electrogram waveform, determining the first position of the first measurement graphic as the position of the feature of the electrogram waveform.

In an embodiment, the method further includes determining the feature of the electrogram waveform using a model trained using training data labeled by an electrophysiologist to generate candidate features of interest for heartbeat data. In an embodiment, determining the feature of the electrogram waveform includes filtering noise of the electrogram waveform using independent component analysis. In an embodiment, the feature of the electrogram waveform is a peak or inflection of the electrogram waveform.

In an embodiment, the method further includes determining a command by processing an audio input from the user; and updating the first position of the first measurement graphic based on the command.

In an embodiment, the method further includes determining proximity between the location of the marker and a target location of the electrogram waveform; and providing audio feedback at a frequency according to the proximity. In an embodiment, the method further includes determining the target location of the electrogram waveform based on a point of activation of a heartbeat signal in the electrogram waveform.

In an embodiment, determining the gaze direction of the user by processing sensor data from the HMD includes determining head tracking information using the sensor data; determining eye tracking information using the sensor data; and determining that the head tracking information is consistent with the eye tracking information.

In an embodiment, the method further includes determining a position of a first surface of an electronic display; and wherein the holographic rendering of intracardiac geometry and the electrogram waveform are displayed by the HMD on a second surface offset from the first surface.

In an embodiment, the method further includes determining a gesture indicating an interaction by the user with the electrogram waveform, wherein the measurement of the electrogram waveform is further determined using the gesture. For example, the gesture is a hand gesture using one or more fingers of the user.

In various embodiments, a system includes a head-mounted display (HMD) worn by a user; and a non-transitory computer-readable storage medium storing instructions, the instructions when executed by one or more processors cause the one or more processors to: provide, for display by the HMD, a holographic rendering of intracardiac geometry including position of a catheter; provide, for display by the HMD, an electrogram waveform generated using data collected from the catheter, wherein the electrogram waveform is displayed adjacent to the holographic rendering; determine a gaze direction of the user by processing sensor data from the HMD; provide, for display by the HMD, a marker overlaid on the electrogram waveform at a location based on an intersection point between the gaze direction and the electrogram waveform; determine a measurement of the electrogram waveform using the location of the marker; and provide, for display by the HMD, the measurement of the electrogram waveform adjacent to the electrogram waveform.

In various embodiments, a method includes providing, for display by a head-mounted display (HMD) worn by a user, a holographic rendering of intracardiac geometry including position of a catheter. The method further includes providing, for display by the HMD, an electrogram waveform generated using data collected from the catheter, wherein the electrogram waveform is displayed adjacent to the holographic rendering. The method further includes determining a gesture indicating an interaction by the user with the electrogram waveform. The method further includes determining a measurement of the electrogram waveform using the gesture. The method further includes providing, for display by the HMD, the measurement of the electrogram waveform adjacent to the electrogram waveform.

In various embodiments, a non-transitory computer-readable storage medium stores instructions that when executed by one or more processors cause the one or more processors to perform steps including any of the methods described herein.

DETAILED DESCRIPTION

Figure 1:
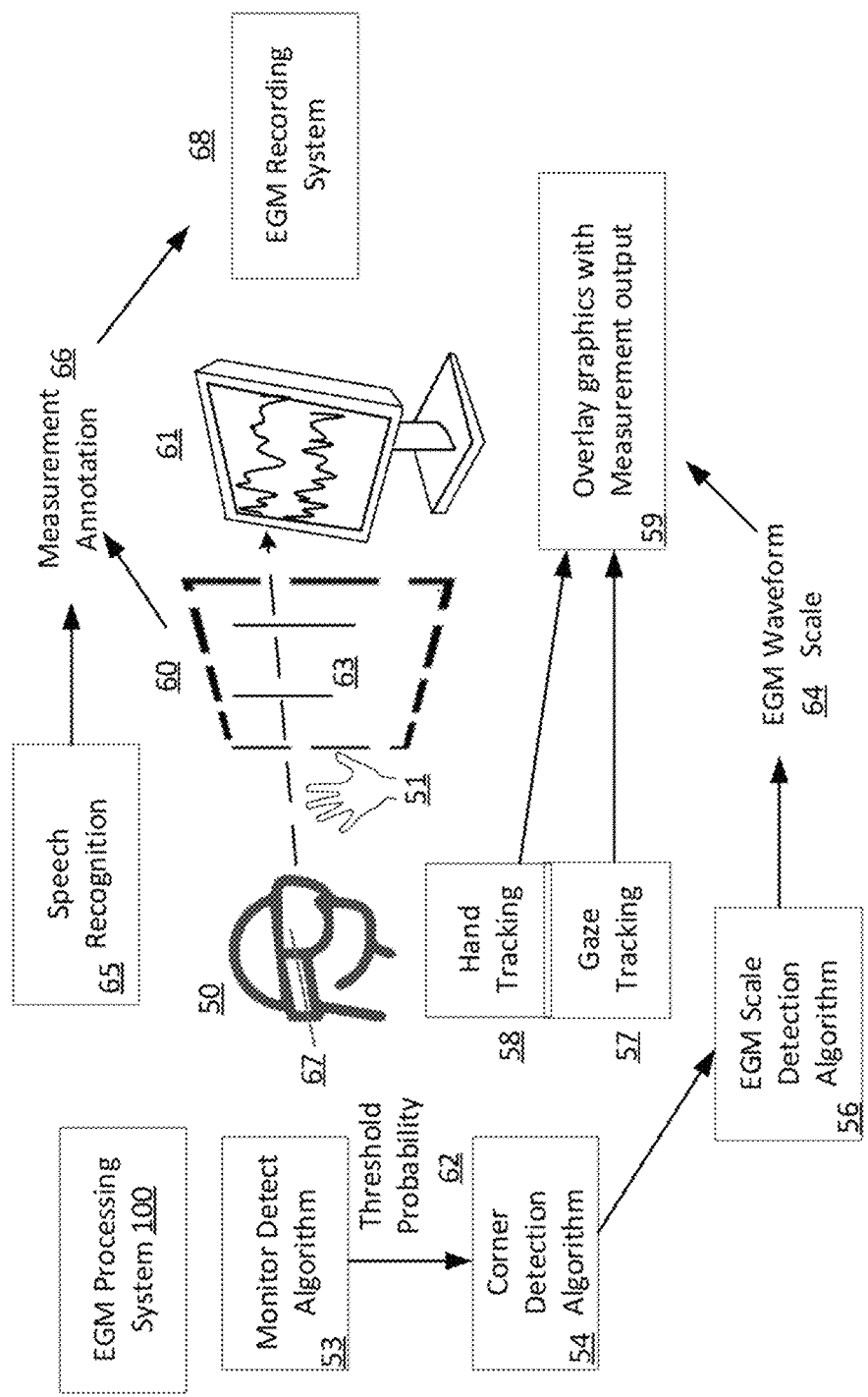
FIG. 1 is an illustration of an EGM processing system including a physical EGM monitor according to one embodiment.

Embodiments of the present invention provide a sterile interface that can be operated seamlessly across multiple medical systems, e.g., to measure and annotate electrogram information. A head-mounted display (HMD) device provides a means for a physician to view and/or interact with EGM information (for example, which would be displayed on 2-dimensional (2D) monitor displays in a conventional system) in a mixed reality or augmented reality environment. In some embodiments, the head-mounted display provides EGM information as being overlaid on a monitor for display to a user or provides EGM information in conjunction with a display on one or more other devices. In other embodiments, the head-mounted display may also provide the EGM information, avoiding the need for monitor displays. The head-mounted display can display graphics such as 3D holographic renderings or other information such as data from sensors or instruments (e.g., catheter).

In some embodiments, an EGM processing system 100 includes one or more HMDs and/or 2D monitor displays, and one or more sources of electrogram data. An HMD may be an augmented reality device, or another type of device, such as virtual reality, mixed reality, or other immersive reality devices. An example HMD is the MICROSOFT HOLOLENS or a modified version of this, for example, equipped with additional sensors or hardware. In other embodiments, the HMD may be a completely custom-designed HMD.

A HMD or computer device may include one or more of: a position/orientation locator for locating its position and orientation in physical space (e.g., 2D or 3D), a wireless interface to communicate information between the devices, one or more processors for processing user input and data, storage for capturing data, a non-transitory computer-readable storage medium storing instructions to execute embodiments of methods described herein, a display, a microphone for capturing audio (e.g., from a user) and detecting spoken commands, a camera for capturing image data, sensors for eye-tracking and/or gaze-tracking, and sensors for detecting hand and/or finger position and pose.

EGM data is displayed by one or more of HMD displays and 2D monitor displays. Display data includes one or more of captured EGM data, user annotations, calculated measurements, and feedback of automatic processing. In one aspect, the EGM 2D monitor display is directly annotated with additional information for display on a conventional 2D monitor display. In another aspect, the EGM 2D monitor display is annotated with additional information in an overlay by the HMD. In another aspect, some or all EGM data and additional information is displayed within the HMD (e.g., without a monitor display).

In various embodiments, user input is achieved through one or more of voice input, gaze input, hand position, hand pose, or automated processing techniques. In one aspect, the user interacts with the system using commands from a predefined vocabulary of commands. In another aspect, the system uses natural language processing (NLP) to interpret general commands from spoken phrases, e.g., "move left 10 milliseconds." In another aspect, gaze input based on head position and orientation and/or eye position and orientation is used to manipulate cursors on a display. In another aspect, one or more of hand and figure position and or pose is used to manipulate cursors on a display.

In another aspect, automated signal processing techniques, e.g., peak detection or waveform classification, provide a means to generate audio cues that aid the physician in interpreting the EGM signals. In one aspect, audio cues are provided that can aid in interpreting the order of events occurring on multiple signals. In another aspect, audio cues provide interpretation of how early a second signal is occurring relative to a reference. Signal processing techniques may also automatically position or assist in positioning of cursors on a display. In another aspect, any number of input techniques may be used in combination to interact with the system, e.g., voice command and gaze direction. These input techniques may be used to generate cursor positions, measurements between cursor positions in pixels, voltage and/or time, and annotations for storage by the system.

I. Example System Environment Including Monitor Display

FIG. 1 is an illustration of an EGM processing system 100 including a physical EGM monitor according to one embodiment. In some embodiments, the EGM processing system 100 can be used for sterile electrogram annotation using existing electrogram monitors, e.g., in a room equipped for surgical procedures. In some embodiments, the EGM recording system 68 produces waveform tracings of electrograms and provides the waveforms to one or more monitors 61 for display. An example of an EGM recording system 68 is the GENERAL ELECTRIC CardioLab Electrophysiology Recording system. The EGM processing system 100 can enable hands-free annotation and employs a HMD 67 with any number of the following characteristics: one or more onboard sensors (e.g., camera or distance sensor, among others) for acquisition of range and image data; ability to produce 3D overlay graphics (e.g., holographic renderings) superimposed on the real world; gaze, eye, and hand tracking capabilities; and one or more microphones or other types of audio sensors for recording annotations provided by audio.

In the embodiment shown in FIG. 1, the HMD 67 acquires an image of a monitor 61 and inputs the acquired image to a Monitor Detect Algorithm 53 that employs computer vision techniques to process the image to detect presence of a physical monitor configured to display EGM information. Example computer vision techniques include but are not limited to Faster R-CNNs (Girshick et al., 2015), You Only Look Once (YOLO) (Redmon and Farhadi, 2015), and Single Shot Detectors (SSDs) (Liu et al., 2015). Such techniques can generate a region and probability that an object is associated with a certain class that a classifier has been trained to recognize. For example, the EGM processing system 100 determines a probability that a region includes at least a portion of an image of a monitor. For any region having a probability greater than a threshold probability 62, the EGM processing system 100 uses a Corner Detection Algorithm 54 to determine the corners of the imaged monitor. The EGM processing system 100 fits the imaged monitor to a model of a size of the object (i.e., monitor) to estimate position in 3D space of a planar rectangle 60 of a surface of the monitor 61. The surface may be a viewing surface of the monitor 61 that displays EGM information. The planar rectangle 60 can be offset by a predetermined distance from the surface such that the graphics displayed on the planar rectangle 60 appear to the user 50 as being superimposed on images displayed by the monitor 61 (e.g., displayed as holograms).

The EGM processing system 100 provides overlay graphics (with measurement output) 59, 63 to the HMD 67 for display to a user 50 such that the overlay graphics 59, 63 appear to be positioned on the planar rectangle 60. The gaze tracking 57, voice tracking, and/or hand tracking 58 capabilities of the HMD 67 are used to position graphics of a digital caliper 63 (e.g., two parallel line cursors that can be positioned relative to the electrograms). The user 50 may use their voice, direct their gaze, and/or move their hand 51 to signal modifications to the positions of the digital calipers 63, which appear superimposed over the EGM waveforms.

In some embodiments, the change in position of the digital calipers 63 when directed by voice, gaze, and/or hand control may switch between detected positions of interest as detected by algorithms on processed electrogram information. The EGM processing system 100 can determine positions of interest using at least waveform statistics including peak detection on an EGM signal or derived signals. The EGM processing system 100 can determine the positions of interest at least in part by recalling previously selected positions by the current user 50 or other users of the EGM processing system 100 through a trained machine learning model.

In the embodiment shown in FIG. 1, the EGM processing system 100 uses an EGM Waveform Scale 64 to convert spacing distance between the digital calipers 63 to a measured interval value in time or voltage. Attributes of the electrogram monitor 61 (e.g., displaying a scale or grid pattern) may be used to automatically estimate the EGM Waveform Scale 64 using an EGM Scale Detection Algorithm 56. The EGM Waveform Scale 64 may also be known a-priori or be input by the user 50 in a calibration step in which the user adjusts the caliper spacing against a known interval of time or voltage. The audio recorded by the HMD 67 can be stored in digital format, or methods for speech recognition 65 may be used to transcribe a measurement annotation 66. The measurement annotation 66 may be transmitted for storage to the EGM recording system 68.

A source of electrogram data may include one or more of: a capture/conversion system for capturing and converting electrogram 2D monitor display signals, an electrical interface for transmitting analog or digital electrogram data, a camera for imaging electrogram displays, and a transmitter/receiver for transmitting and receiving user input information with the electrogram system. In some embodiments, a system for capturing electrogram data includes one or more catheters. The electrogram data can be transmitted to an HMD or another device for processing or display.

EGM data is integrated into the EGM processing system 100 through one or more means. In one aspect, the EGM processing system 100 can directly measure EGM signals through an analog-to-digital (A/D) converter for processing by the system. In another aspect, the EGM processing system 100 can receive and transmit EGM data from existing EGM recording systems through a predefined hardware and/or software interface, e.g., RS-232, TCP/IP, etc. In another aspect, the EGM processing system 100 can capture EGM recording system 2D monitor display output through one or more capture devices, including directly sampling the monitor signal, or imaging the monitor signal using an imaging camera. EGM waveform data, EGM cursor data and measurements, and EGM parameters may be extracted from the sensed image data. In various embodiments, the EGM processing system 100 can use existing configuration data available or established during system installation, including 2D monitor display layout and placement, electrogram application or hardware configuration, electrogram signal color configuration, placement on 2D monitor displays, and electrogram sweep configurations.

II. Example System Environment without Monitor Display

Figure 2:
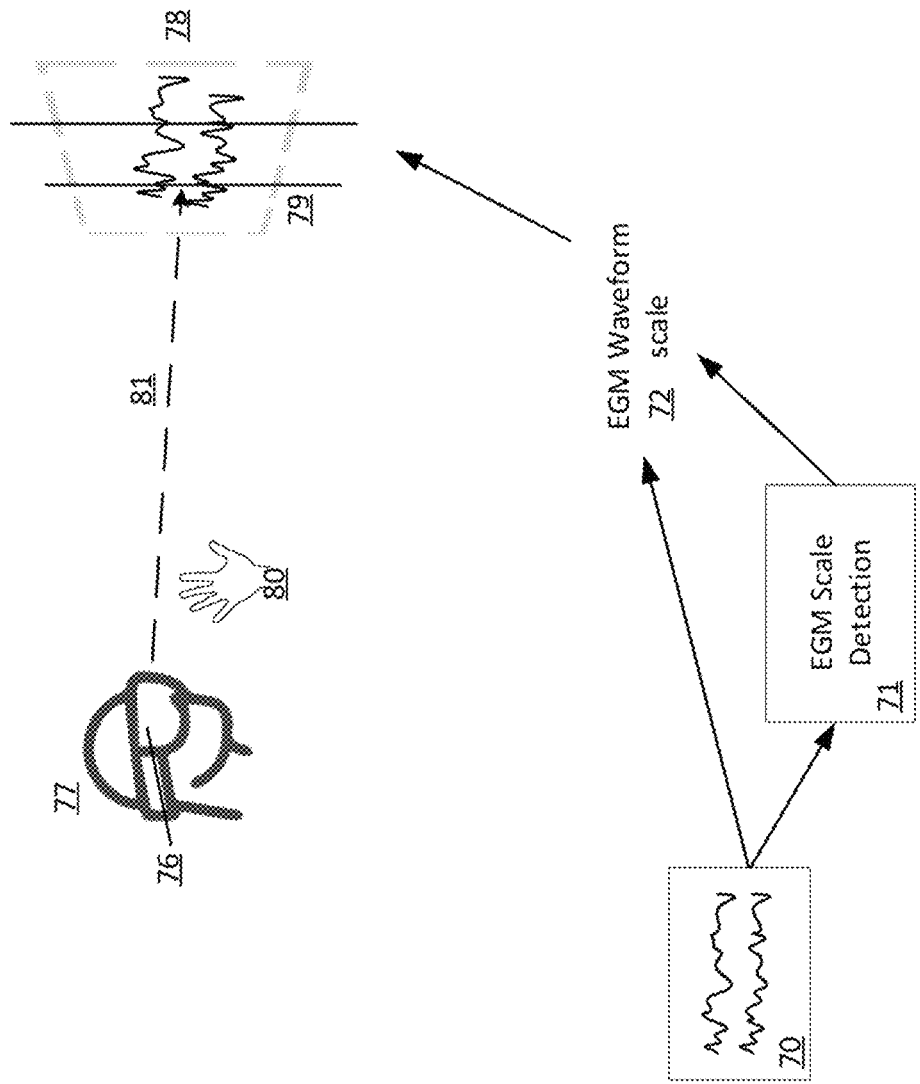
FIG. 2 is an illustration of an EGM processing system using waveform acquisition and display thereof according to one embodiment.

FIG. 2 is an illustration of the EGM processing system 100 using waveform acquisition and display thereof according to one embodiment. As shown in the embodiment of FIG. 2, the EGM processing system 100 can use either a frame grabber or signal acquisition to acquire electrogram information. In one aspect, the EGM signals 70 may be acquired via a frame grabber that acquires a video frame from the video monitor of an existing electrogram system. In another aspect, EGM signals 70 are transmitted via a connection to an EGM recording system that can communicate EGM signals digitally. In another aspect, EGM signals 70 are sampled directly by one or more A/D amplifiers.

An example EGM recording system that can both transmit signals digitally and display the signals (e.g., on a video monitor) is the GENERAL ELECTRIC Cardiolab Electrophysiology Recording System. If the signals are acquired via frame grabber, there is an additional EGM Scale Detection 71 step to determine the time and EGM Waveform Scale 72 (e.g., voltage scale) of the electrogram; this step can be automatically performed using computer vision techniques that extract electrogram data and detect the sweep speed. Alternatively, the user 77 can calibrate the EGM Waveform Scale 72 manually by indicating the length of time and/or voltage of a known measurement.

The waveform 78 is displayed for the user 77 by the HMD 76 as either an image (in the case of a video grabbed frame) or as a line drawing for each imported waveform (in the case of analyzed video frame, digital API, or digital A/D signals). The HMD 76 positions a pair of digital calipers 79 that can be manipulated by a hand 80 of the user 77, voice of the user 77, and/or gaze direction 81 of the user 77. The position of the digital calipers 79 can be adjusted as well as the distance between the digital calipers 79. In some embodiments, the HMD 76 displays the waveform 78 as a holographic image.

In some embodiments, the HMD 76 uses the EGM Waveform Scale 72 to convert the virtual distance between the digital calipers 79 to time (e.g., horizontal axis) or voltage (e.g., vertical axis) and displays these measurements alongside the digital calipers 79 for reference. In some embodiments, additional data associated with the waveform 78 from any number of EGM channels from the current time sample or previous time samples may be displayed with any number of offsets in the vertical, horizontal, or depth direction with respect to the HMD 76.

III. Audio Feedback

Figure 3:
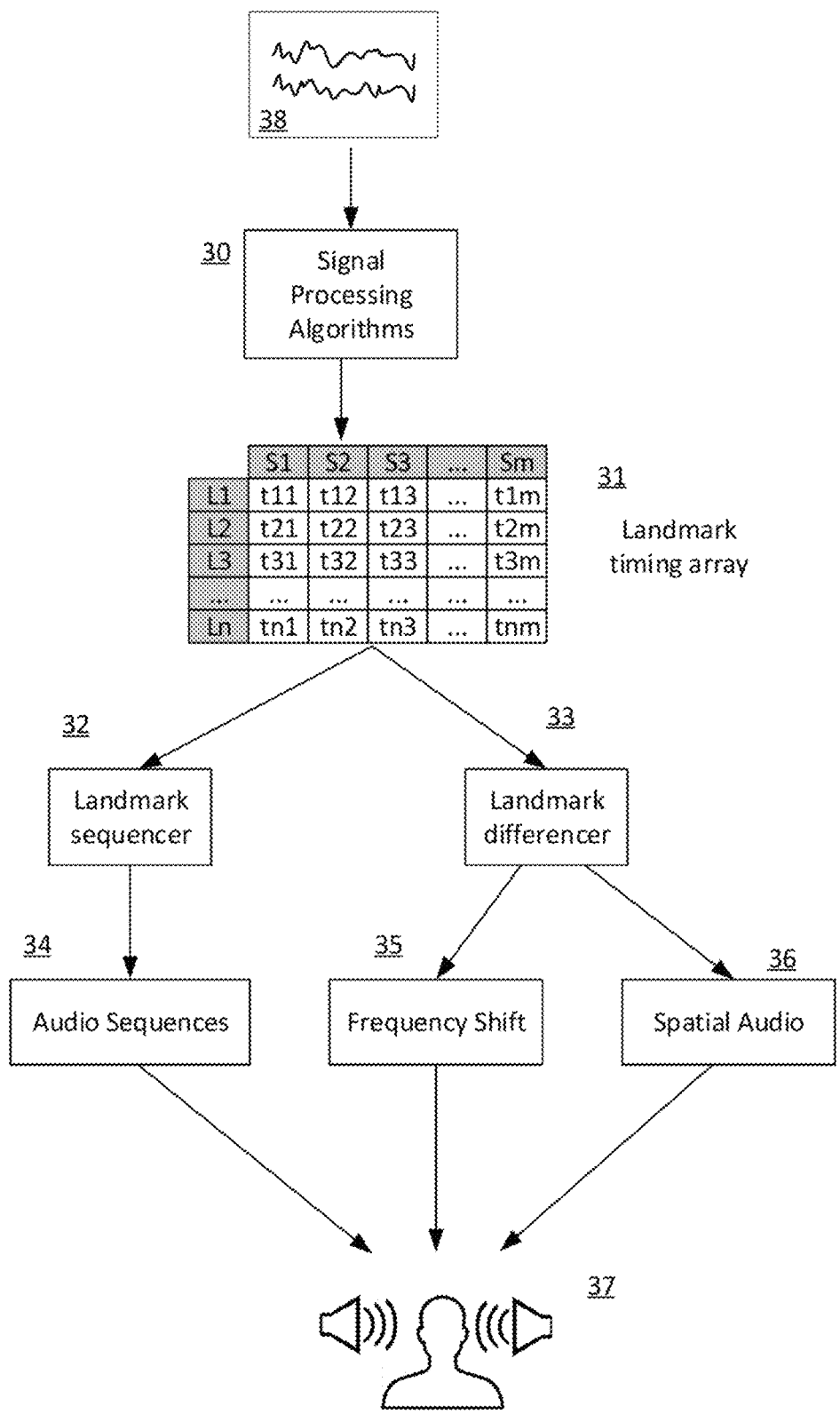
FIG. 3 illustrates audio encoding of signal landmarks according to one embodiment.

FIG. 3 illustrates audio encoding of signal landmarks according to one embodiment. As shown in the embodiment of FIG. 3, the EGM processing system 100 can generate auditory information to serve as a supplement to the raw visual information provided by the EGM signals. The EGM processing system 100 processes the EGM signal information 38 using signal processing algorithms 30 to determine a series of landmark positions on each signal. This results in a landmark timing array 31 that has columns for each signal (e.g., S1, S2, S3, . . . ) and rows (e.g., L1, L2, L3, . . . ) with entries indicating the time that the particular landmark was found in the corresponding signal. It is also possible that one or more landmarks may not be identified in one or more of the signals, in which case those entries are identified as empty.

In various embodiments, the EGM processing system 100 inputs the landmark timing array 31 into algorithms (e.g., landmark sequencer 32 and/or landmark differencer 33) to convert the landmark information into audio information. The landmark sequencer 32 converts similar landmarks into audio sequences 34 of tones that are played sequentially in time, where each tone represents a different signal. The HMD can play the audio sequences 34 using speakers or any other suitable type of audio transmitter. Thus, a user 37 may perceive auditorily the order in which similar events are occurring on multiple signals, or if a landmark entry is empty, the lack of audio for the corresponding signal.

The landmark differencer 33 converts times between successive landmarks or times between neighboring signals into frequency shift information that is played as an audio frequency shift 35 to the user 37. Alternatively, the frequency shift information may be converted into spatial audio 36 such that the user 37 perceives auditorily that a sound is coming from a particular direction (e.g., left, right, or in front of the user) depending on the time difference. The HMD can play the audio frequency shift 35 or spatial audio 36 using speakers or any other suitable type of audio transmitter.

IV. Waveform Timescale

Figure 4:
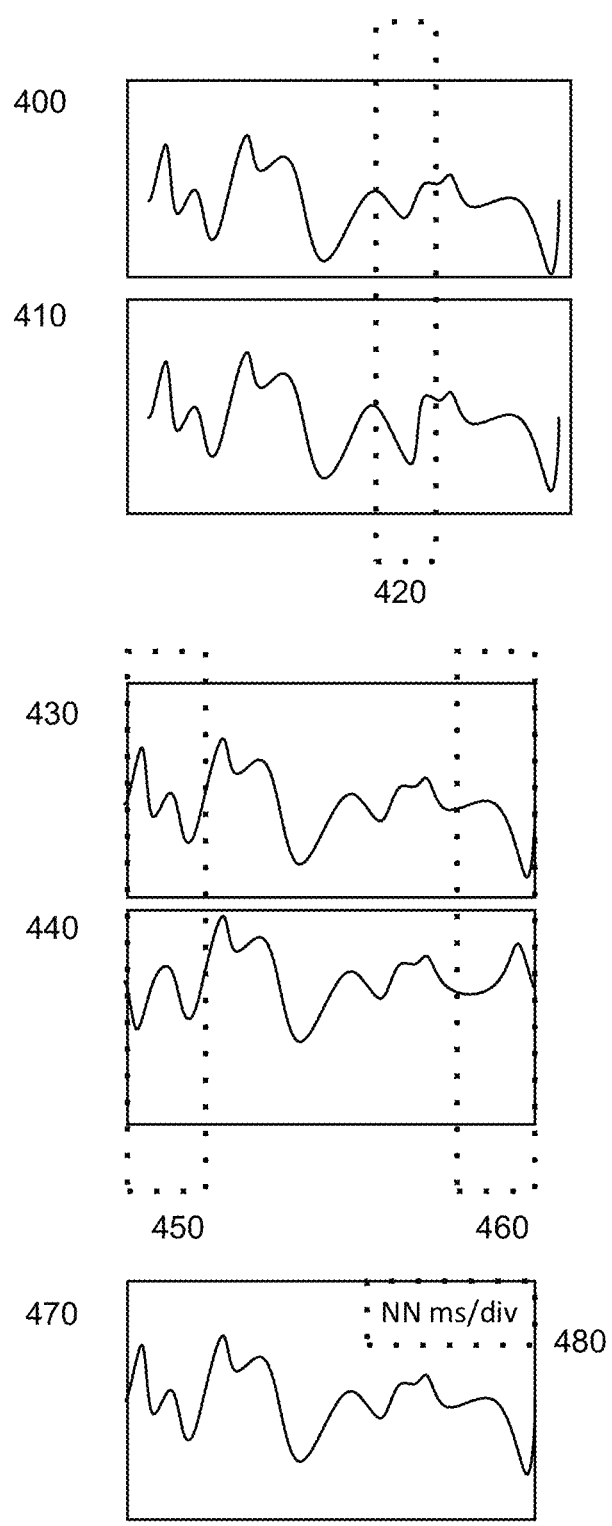
FIG. 4 illustrates a process for determining time scale of a waveform according to one embodiment.

FIG. 4 illustrates a process for determining time scale of a waveform according to one embodiment. As shown in the embodiment of FIG. 4, two waveforms are obtained from a video frame grabber. Electrogram recording systems can represent the electrogram waveforms as a continuously updating waveform that is traced from left to right as the waveform is acquired. When the acquired waveform reaches the right-hand side of the display, the electrogram recording system renews the waveform at the left-hand side and replaces the old waveform as the new waveform traces across.

Image 400 represents a first example image frame acquired from an electrogram recording system at time T1, and image 410 represents a second example image frame acquired at time T2 after time T1. In some embodiments, the difference between time frames (T2−T1) must be less than the time required to perform a complete trace. A suitable computer algorithm can scan images 400 and 410 and find the regions where the waveforms are identical (e.g., or within a threshold difference of amplitude), and the rectangular region 420, where the waveforms are not identical (e.g., deviating at least by the threshold difference of amplitude). The width W in pixels of the region 420 represents how many pixels are swept in the time T2−T1, yielding a sweep speed scale of W/(T2−T1) pixels/second.

Images 430 and 440 illustrate an example case where the waveform sweep has returned to the left side in the time between frame acquisitions. In such a case, both rectangular region 450 with width W1 and rectangular region 460 with width W2 are identified where the waveforms differ between images 430 and 440, and the sweep speed scale calculation becomes (W1+W2)/(T2−T1) pixels/second.

In some embodiments, an electrogram recording system directly display the sweep speed in a fixed position on the video monitor. Image 470 shows an alternative method that may be employed to compute the sweep speed scale, in the case where the acquired frame explicitly displays the sweep speed in a sub-region 480. In such a case, the sub-region 480 is compared against a set of template images, each of which corresponds to a different sweep speed setting. The EGM processing system 100 can determine a template image match as measured by image correlation and use the template image match to establish the sweep speed scale. Other optical character recognition techniques known to one skilled in the art can also be employed to decode the sweep speed information displayed within the embedded character sub-region 480.

V. Example User Interfaces

Figure 5A:
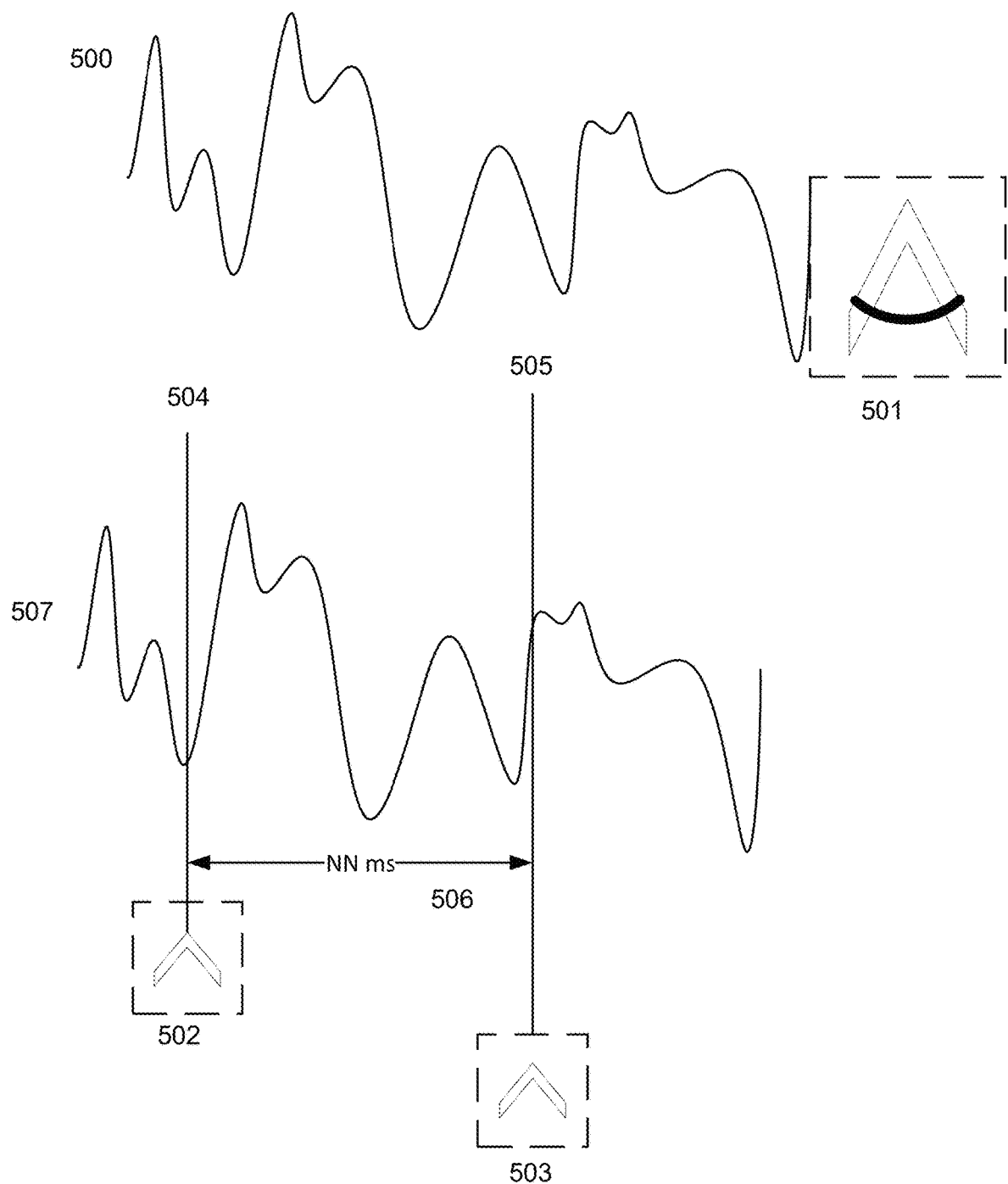
FIG. 5A is a diagram of a gesture-based user interface according to one embodiment.

FIG. 5A is a diagram of a gesture-based user interface according to one embodiment. FIG. 5 shows an embodiment for a gesture-based user interface to control measurement of an electrogram interval. An electrogram 500 is displayed by the EGM processing system 100, via either an HMD or a monitor. The HMD can display an interaction area 501 overlaid on or adjacent to the electrogram 500. The interaction area 501 provides a digital caliper feature for determining measurements of the electrogram 500. In the example shown in FIG. 5, the digital caliper includes graphical representation and a bounding region.

In an embodiment, the HMD tracks the user's finger positions, e.g., to detect and track the thumb position and/or one or more finger positions of the user. Responsive to determining that a finger position is within the rectangular bounding region, the HMD changes the digital caliper feature appearance to indicate that the feature is activated. Once activated, the HMD displays two separately controllable caliper graphics. The left caliper graphic consists of a measurement graphic (e.g., a line) 504 and active area 502. The right caliper graphic consists of a measurement graphic 505 and active area 503. The measurement graphics 504 and 505 are positioned over one or more displayed waveforms along with active areas 502 and 503.

Responsive to determining that the distance between a tracked thumb and another tracked finger is within a threshold distance, and the midpoint position between the tracked thumb and other finger is within the active area 502 or 503, the EGM processing system 100 updates the position of the graphic. Suitable thresholds can be established such that the user perceives that the user is virtually grabbing the digital caliper graphics for manipulation, e.g., moving the digital caliper graphics right and/or left. As the distance between the measurement graphics (e.g., lines) 504 and 505 changes, the displayed measurement 506 updates to indicate the time elapsed between the two lines as represented by the waveform 507. In some embodiments, the active areas 502 and 503 are displaced vertically (or otherwise modified) so that they do not overlap with each other when the displayed measurement 506 becomes small.

VI. Landmark Defection

Figure 6:
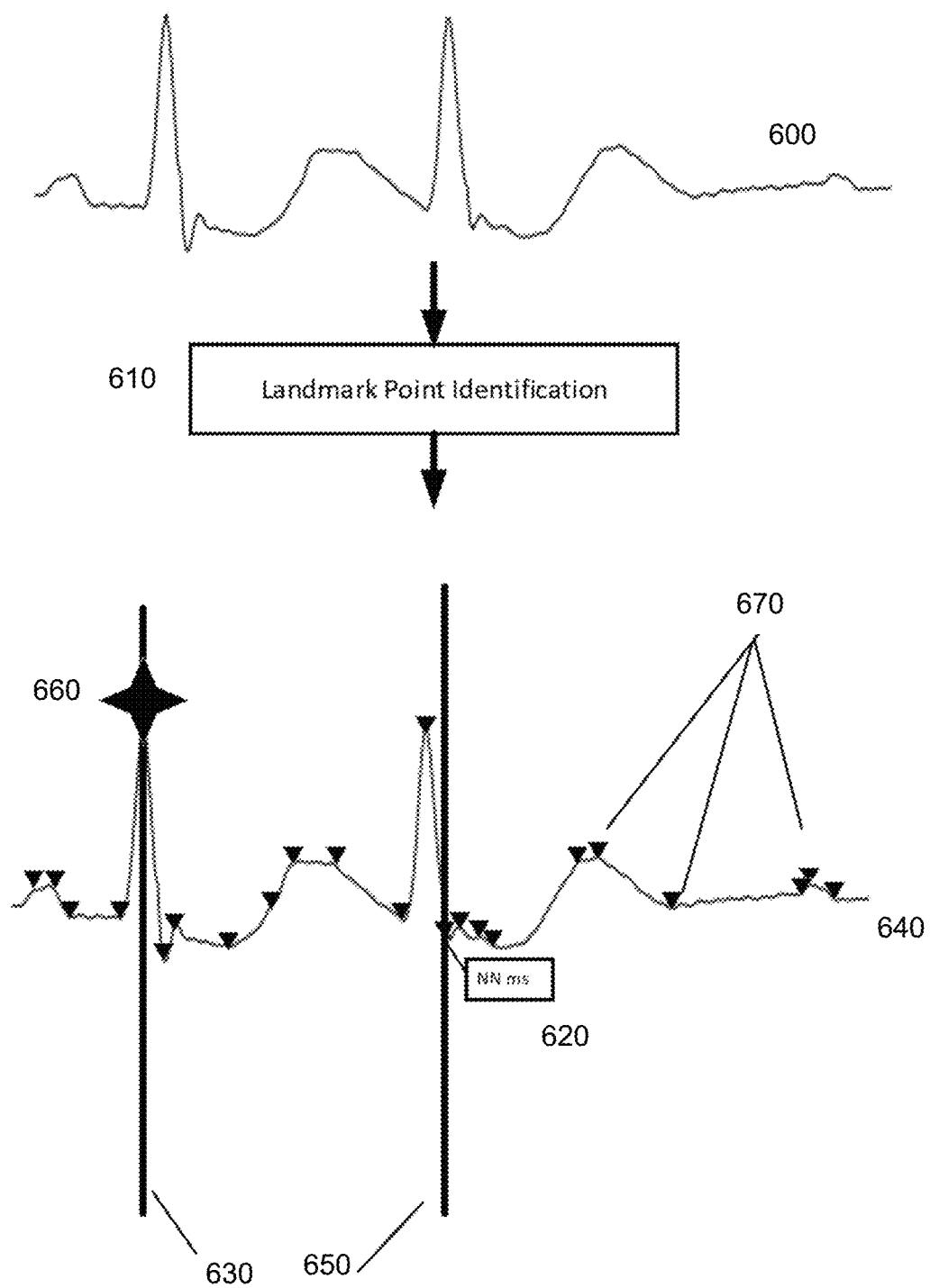
FIG. 6 illustrates a process for determining landmark points in a gaze-based user interface according to one embodiment.

FIG. 6 illustrates a process for determining landmark points in a gaze-based user interface according to one embodiment. FIG. 6 illustrates measurement information as the user's gaze moves across a waveform. The EGM processing system 100 processes waveform 600 using a Landmark Point Identification 620 algorithm to identify likely points of interest on the waveform, that is, landmarks. The Landmark Point Identification 620 algorithm can be constructed by combining elements of one or more of thresholded peak finding, derivative calculation to find points of inflection (e.g., based on maximum derivative), piecewise linear approximation to find suitable inflection points above an error threshold, and morphological techniques to identify landmarks in signals.

An example Landmark Point Identification 620 algorithm for an input electrogram signal 600 includes the following steps: bandpass filter to eliminate DC and frequencies above 100 Hz; determine the maximum of a first region of points above a threshold voltage as a reference point; compute derivative of signal; identify positions in the signal where derivative changes sign; scan through the signal, constructing line segments that best fit the signal within an error threshold; and add endpoints of the line segments to the set of identified positions. An example of one such scan along algorithm can be found in Ishijima, M., Shin, S. B., Hostetter, G. H. & Sklansky, J., *Scan along polygon approximation for data compression of electrocardiograms*, 30 IEEE TRANS. BIOMED. ENG. 723-29 (1983).

In various embodiments, the positions identified by the Landmark Point Identification 620 algorithm become the set of landmarks (e.g., interesting positions). The landmarks and the reference point, represented by the triangle positions 670 and star 660, respectively, are overlaid across the signal 640. Other combinations of techniques can be used to identify the set of landmark positions. The landmark positions 670 and 660 represent the set of measurement positions that the user's gaze is attracted to for interactive measurement. The signal can also be presented as a graphic by the HMD without graphical markers (e.g., the triangles 670 and star 660) so that the user with HMD can inspect the signal without visual clutter. The waveform graphic is represented on a plane oriented so that the waveform graphic is presented on a vertical plane that faces toward the user's gaze, a technique referred to as billboarding. The HMD can also display a measurement graphic 630 for a digital caliper feature, as previously described.

In some embodiments, the user's gaze direction is provided by the HMD as the equation of a ray emanating from the user's head in the direction of gaze. The ray information is input to a processor, along with the equation of the plane and positions of the waveform landmark points on the plane. The EGM processing system 100 determines intersection of the ray with the plane on which the waveform graphics are displayed. In an embodiment, the EGM processing system 100 determines the distance between the intersection point with each landmark point and determines the landmark point associated with the minimum distance. Responsive to determining that the minimum distance is below a threshold, the HMD displays a measurement graphic 650 that identifies the landmark (e.g., a point on the signal 640); the waveform time distance between measurement graphic 630 and measurement graphic 650 is shown in a measurement 620.

In various embodiments, signal processing techniques are employed to identify landmark positions on the signal. The landmarks can be used to automatically position a measurement cursor at the identified landmarks, or alternatively, as input to algorithms that generate audio from the landmark sequencing. Examples of signal processing techniques include but are not limited to: thresholded peak finding to determine the lowest or highest point in a region above/below some threshold voltage; thresholded slope finding to determine points at the center of where the slope of the signal increases above a given threshold, or where there is an inflection point; wavelet based methods such as described in Paul S Addison, *Wavelet transforms and the ECG: a review*, 26 PHYSIOL. MEAS. R155-R199 (2005), which can be used to identify portions of the signals with interesting characteristics; and piece-wise linear approximations such as described in Eamonn Keogh, Selina Chu, David Hart & Michael Pazzani, *Segmenting Time Series: A Survey and Novel Approach*, in DATA MINING IN TIME SERIES DATABASES 1-21 (2003), which can be used to identify change points of interest in the signal.

VII. Example Process Flow

Figure 5B:
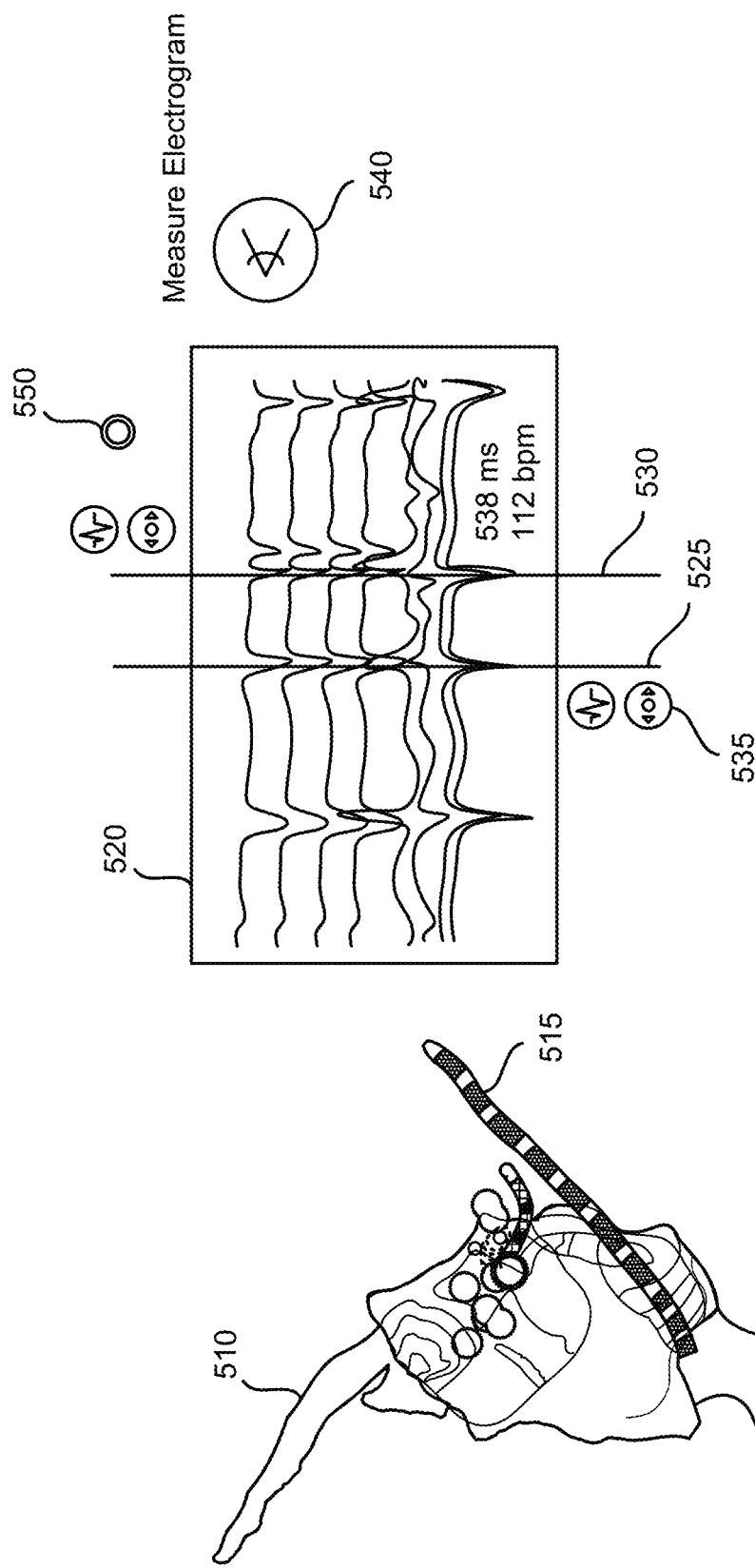
FIG. 5B is an example user interface displayed by a head-mounted display according to one embodiment.
Figure 7:
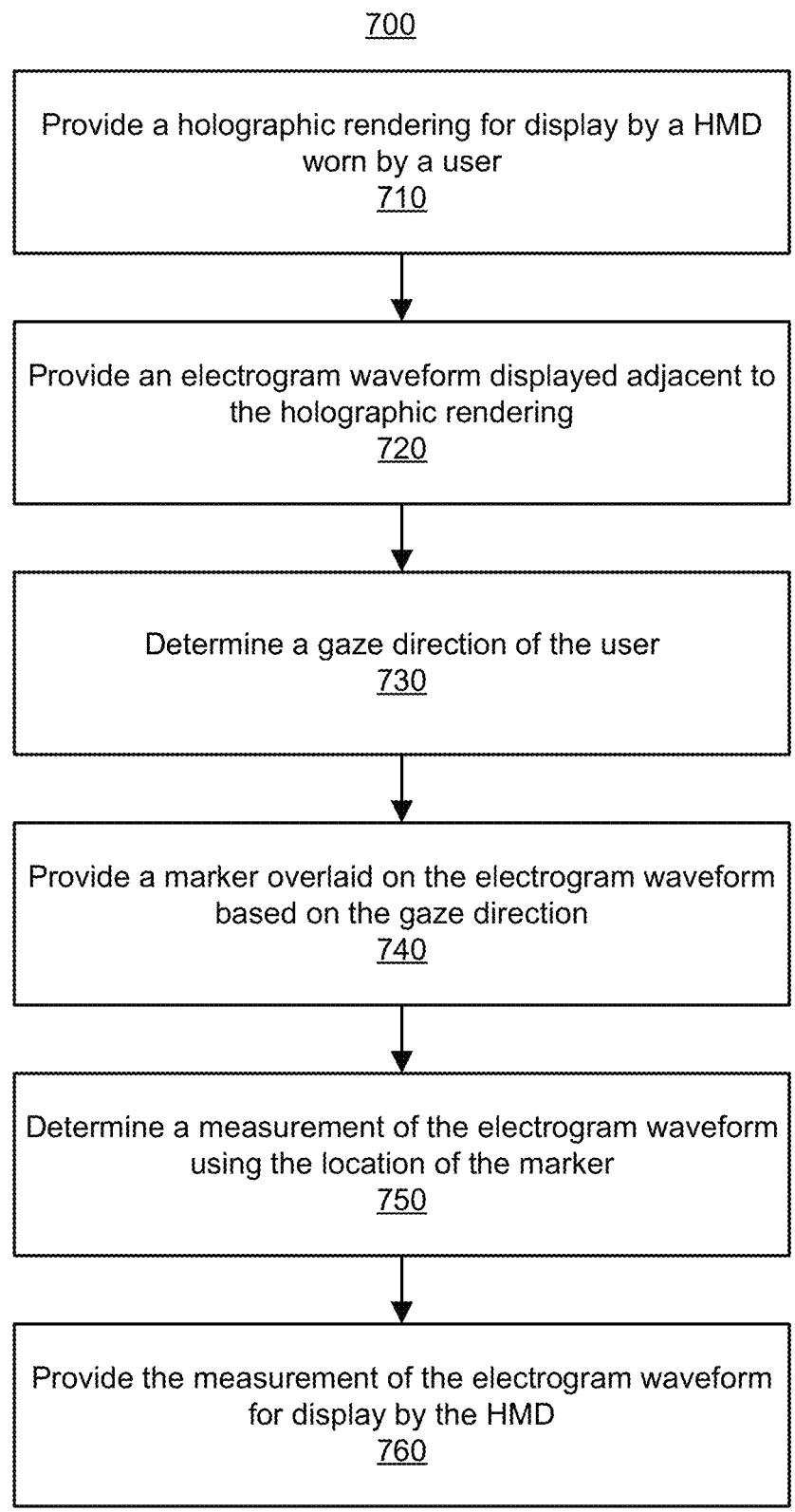
FIG. 7 is a flowchart of a method for displaying EGM information according to one embodiment.

FIG. 7 is a flowchart of a method 700 for displaying EGM information according to one embodiment. The method 700 is described with reference to FIG. 5B. FIG. 5B is an example user interface displayed by a head-mounted display according to one embodiment. The example user interface shown in FIG. 5B includes a holographic rendering 510 and an electrogram waveform 520, which may be displayed adjacent to each other. In various embodiments, the EGM processing system 100 provides graphics for display by the HMD at a frame rate of at least 30 frame per second; the EGM processing system 100 also achieves a latency under 50 milliseconds between EGM signal acquisition and display. This frame rate and latency helps to provide visual comfort to a user wearing the HMD and interacting with the user interface.

The EGM processing system 100 provides 710 a holographic rendering 510 for display by the HMD worn by the user. The holographic rendering 510 shows intracardiac geometry, for example, of a patient's heart during a procedure to assist an operating surgeon. The holographic rendering 510 also includes display of a catheter 515. The HMD can update the holographic rendering 510 to reflect changes in the position or orientation of the catheter 515 (e.g., in real time). Based on user input, the HMD can also update the intracardiac geometry, for example, by rotating, translating, increasing or decreasing zoom, changing color-coding, changing transparency of certain portions, among other changes to the displayed visual.

The EGM processing system 100 provides 720 an electrogram waveform 520 for display by the HMD; the electrogram waveform 520 is displayed adjacent to the holographic rendering 510 such that both are in the field of view of the user (e.g., allowing simultaneous viewing of both parts of the user interface). The electrogram waveform 520 includes one or more signals generated using data collected by the catheter 515 or other sensors or instruments.

The EGM processing system 100 determines 730 a gaze direction of the user. The EGM processing system 100 tracks the user's head direction and eye direction using sensor data from the HMD. The EGM processing system 100 can determine that head tracking information is consistent with eye tracking information. For example, the EGM processing system 100 verifies that the user's head direction is within a threshold error from the user's eye direction. The EGM processing system 100 determines the user's gaze direction using the head direction and eye direction, e.g., by verifying one with the other to remove false positive directions or determining the average between the two directions to provide a more stable gaze direction. In other embodiments, the EGM processing system 100 determines the user's gaze direction using only one of: head direction and eye direction.

The EGM processing system 100 provides 740 a marker 550 overlaid on the electrogram waveform 520 based on the gaze direction. In various embodiments, the HMD displays the marker 550 overlaid on the electrogram waveform 520 at an intersection between the gaze direction and the electrogram waveform; for example, the intersection between a line of the gaze direction and a planar surface on which the electrogram waveform is displayed in a 3D space. As the user's gaze direction changes, the EGM processing system 100 can update the location of the displayed marker 550 (e.g., in real time). By controlling the marker 550, the user can interact hands-free with the user interface. The EGM processing system 100 provides a technical solution, that is, hands-free interaction of the user interface via an HMD, to the previously described problem of users (e.g., physicians or surgeons) not being able to—or having inconvenience to—touch a physical user interface in a sterile environment for a interventional procedure. Moreover, by displaying information to the user via the HMD, the user's view of the information is not hindered due to other obstructions. The user also does not need to look at multiple monitor displays for intracardiac geometry and electrogram waveform information, as the HMD can display both adjacent to one another.

The EGM processing system 100 determines 750 a measurement of the electrogram waveform 520 using the location of the marker. For example, the EGM processing system 100 determines the measurement using a digital caliper. Responsive to determining that the marker 550 is navigated to the measure electrogram 540 graphic, the EGM processing system 100 determines that the user intends to take a measurement using the digital caliper; and the EGM processing system 100 displays a first measurement graphic 525 and a second measurement graphic 530. Responsive to determining that the marker 550 is navigated to the control graphic 535 of the first measurement graphic 525, the EGM processing system 100 determines that the user intends to change the position of the first measurement graphic 525. The EGM processing system 100 updates the position of the first measurement graphic 525 by tracking the user's gaze direction, for instance, indicating a shift of the first measurement graphic 525 to the left or right along the x-axis (i.e., time) of the electrogram waveform 520. In a similar manner, the EGM processing system 100 can update the position of the second measurement graphic 530. The EGM processing system 100 determines the measurement of the electrogram waveform 520 based on a distance between position of the first measurement graphic 525 the position of the second measurement graphic 530.

In some embodiments, the EGM processing system 100 automatically adjusts position of the measurement graphics. For example, responsive to determining that a position of the first measurement graphic 525 is within a threshold distance from a position of a feature of the electrogram waveform 520, the EGM processing system 100 updates the position of the first measurement graphic 525 to the position of the feature. In some embodiments, the EGM processing system 100 determines the feature of the electrogram waveform 520 using a model. For example, the model is trained using training data labeled by an electrophysiologist to generate candidate features of interest (e.g., landmarks) for heartbeat data or a QRS complex of a heartbeat. Features of the electrogram waveform can be a peak or inflection of the electrogram waveform. The features can be determined using independent component analysis, beat-to-beat amplitude, separate analyses of high- and low-frequency wavelet components, wavelength-based analysis, and timing intervals, among other methods. In an embodiment, the EGM processing system 100 filters noise of the electrogram waveform 520 by using independent component analysis, identifying information-rich portions of a signal (e.g., including heartbeat related landmarks), or using other types of signal processing techniques known to one skilled in the art. The The EGM processing system 100 provides 760 the measurement of the electrogram waveform 520 for display by the HMD. The measurement can be displayed adjacent to a portion of, or overlapping a portion of, the electrogram waveform 520. The EGM processing system 100 can update the measurement responsive to change to position of a measurement graphic and thus the distance between measurement graphics.

In an embodiment, the EGM processing system 100 determines a position of a first surface of an electronic display (e.g., a monitor display). The HMD provides the holographic rendering 510 and the electrogram waveform 520 displayed on a second surface offset from the first surface. As a result, the holographic rendering 510 and the electrogram waveform 520 appear as floating-in-the-air holograms from the perspective of the user wearing the HMD.

In some embodiments, the EGM processing system 100 also uses voice commands from the user. The EGM processing system 100 determines a voice command by processing an audio input from the user. Example commands include "take a picture" or "move it a millisecond earlier." Responsive to determining that user intends to "take a picture" of the electrogram waveform 520, the EGM processing system 100 captures and stores an image of the current display of the electrogram waveform 520, the holographic rendering 510, and/or displayed measurements (e.g., from the digital calipers) or other annotations. Responsive to determining that the user intends to "move it a millisecond earlier," referring to position of a measurement graphic, the EGM processing system 100 updates the position of the measurement graphic according to the instruction. The EGM processing system 100 can use any number of natural language processing techniques to determine voice commands. In some embodiments, the EGM processing system 100 uses a database of simplified vocabulary, which are associated with a set of known commands for interacting with a user interface.

In some embodiments, the EGM processing system 100 provides audio feedback to the user. As an example, the EGM processing system 100 determines proximity between the location of the marker 550 and a target location of the electrogram waveform 520 (e.g., of a landmark). In some embodiments, the EGM processing system 100 determines the target location based on a point of activation of a heartbeat signal in the electrogram waveform 520. The EGM processing system 100 provides audio feedback at a frequency according to the proximity. For instance, the audio feedback (e.g., a beeping sound or a tone) is provided at a higher frequency as the proximity decreases and at a lower frequency as the proximity increases. In other embodiments, the EGM processing system 100 determines proximity between the target location and position of a measurement graphic (e.g., 525 or 530 shown in FIG. 5) instead of the location of the marker 550.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:
1. A system comprising:
a head-mounted display (HMD) worn by a user; and
a non-transitory computer-readable storage medium storing instructions, the instructions when executed by one or more processors cause the one or more processors to:
provide, for display by the HMD, a holographic rendering of intracardiac geometry including position of a catheter;
provide, for display by the HMD, an electrogram waveform generated using data collected from the catheter, wherein the electrogram waveform is displayed adjacent to the holographic rendering;
determine a gaze direction of the user by processing sensor data from the HMD;
provide, for display by the HMD, a marker overlaid on the electrogram waveform at a location based on an intersection point between the gaze direction and the electrogram waveform;
determine a first position of a first measurement graphic by tracking the location of the marker;
determine a second position of a second measurement graphic by tracking the location of the marker;
determine a measurement of the electrogram waveform based on a distance between the first position and the second position; and
provide, for display by the HMD, the measurement of the electrogram waveform adjacent to the electrogram waveform.

2. The system of claim 1, wherein the non-transitory computer-readable storage medium stores further instructions that when executed by the one or more processors cause the one or more processors to:
determine a feature of the electrogram waveform; and
responsive to determining that the first position of the first measurement graphic is within a threshold distance from a position of the feature of the electrogram waveform, determine the first position of the first measurement graphic as the position of the feature of the electrogram waveform.

3. The system of claim 2, wherein the non-transitory computer-readable storage medium stores further instructions that when executed by the one or more processors cause the one or more processors to:
determine the feature of the electrogram waveform using a model trained using training data labeled by an electrophysiologist to generate candidate features of interest for heartbeat data.

4. The system of claim 1, wherein the non-transitory computer-readable storage medium stores further instructions that when executed by the one or more processors cause the one or more processors to:
determine a command by processing an audio input from the user; and
update the first position of the first measurement graphic based on the command.

5. The system of claim 1, wherein determine the gaze direction of the user by processing sensor data from the HMD comprises:
determine head tracking information using the sensor data;
determine eye tracking information using the sensor data; and
determine that the head tracking information is consistent with the eye tracking information.

6. A method comprising:
providing, for display by a head-mounted display (HMD) worn by a user, a holographic rendering of intracardiac geometry including position of a catheter;

providing, for display by the HMD, an electrogram waveform generated using data collected from the catheter, wherein the electrogram waveform is displayed adjacent to the holographic rendering;
determining a gaze direction of the user by processing sensor data from the HMD;
providing, for display by the HMD, a marker overlaid on the electrogram waveform at a location based on an intersection point between the gaze direction and the electrogram waveform;
determining a first position of a first measurement graphic by tracking the location of the marker;
determining a second position of a second measurement graphic by tracking the location of the marker;
determining a measurement of the electrogram waveform based on a distance between the first position and the second position; and
providing, for display by the HMD, the measurement of the electrogram waveform adjacent to the electrogram waveform.

7. The method of claim 6, further comprising:
determining a feature of the electrogram waveform; and
responsive to determining that the first position of the first measurement graphic is within a threshold distance from a position of the feature of the electrogram waveform, determining the first position of the first measurement graphic as the position of the feature of the electrogram waveform.

8. The method of claim 7, further comprising:
determining the feature of the electrogram waveform using a model trained using training data labeled by an electrophysiologist to generate candidate features of interest for heartbeat data.

9. The method of claim 7, wherein determining the feature of the electrogram waveform comprises:
filtering noise of the electrogram waveform using independent component analysis.

10. The method of claim 7, wherein the feature of the electrogram waveform is a peak or inflection of the electrogram waveform.

11. The method of claim 6, further comprising:
determining a command by processing an audio input from the user; and
updating the first position of the first measurement graphic based on the command.

12. The method of claim 6, further comprising:
determining proximity between the location of the marker and a target location of the electrogram waveform; and
providing audio feedback at a frequency according to the proximity.

13. The method of claim 12, further comprising:
determining the target location of the electrogram waveform based on a point of activation of a heartbeat signal in the electrogram waveform.

14. The method of claim 6, wherein determining the gaze direction of the user by processing sensor data from the HMD comprises:
determining head tracking information using the sensor data;
determining eye tracking information using the sensor data; and
determining that the head tracking information is consistent with the eye tracking information.

15. The method of claim 6, further comprising:
determining a position of a first surface of an electronic display; and
wherein the holographic rendering of intracardiac geometry and the electrogram waveform are displayed by the HMD on a second surface offset from the first surface.

16. The method of claim 6, further comprising:
determining a gesture indicating an interaction by the user with the electrogram waveform, wherein the measurement of the electrogram waveform is further determined using the gesture.

17. A non-transitory computer-readable storage medium storing instructions, the instructions when executed by one or more processors cause the one or more processors to:
provide, for display by a head-mounted display (HMD) worn by a user, a holographic rendering of intracardiac geometry including position of a catheter;
provide, for display by the HMD, an electrogram waveform generated using data collected from the catheter, wherein the electrogram waveform is displayed adjacent to the holographic rendering;
determine a gaze direction of the user by processing sensor data from the HMD;
provide, for display by the HMD, a marker overlaid on the electrogram waveform at a location based on an intersection point between the gaze direction and the electrogram waveform;
determine a first position of a first measurement graphic by tracking the location of the marker;
determine a second position of a second measurement graphic by tracking the location of the marker;
determine a measurement of the electrogram waveform based on a distance between the first position and the second position; and
provide, for display by the HMD, the measurement of the electrogram waveform adjacent to the electrogram waveform.

18. A method comprising:
providing, for display by a head-mounted display (HMD) worn by a user, a holographic rendering of intracardiac geometry including position of a catheter;
providing, for display by the HMD, an electrogram waveform generated using data collected from the catheter, wherein the electrogram waveform is displayed adjacent to the holographic rendering;
determining a gesture indicating an interaction by the user with the electrogram waveform to control a location of a marker;
determining a first position of a first measurement graphic by tracking the location of the marker;
determining a second position of a second measurement graphic by tracking the location of the marker;
determining a measurement of the electrogram waveform based on a distance between the first position and the second position; and
providing, for display by the HMD, the measurement of the electrogram waveform adjacent to the electrogram waveform.

* * * * *